US00PP26187P2

(12) United States Plant Patent
Yam

(10) Patent No.: US PP26,187 P2
(45) Date of Patent: Dec. 1, 2015

(54) ***CALATHEA* PLANT NAMED 'FUSION WHITE'**

(50) Latin Name: *Calathea leitzei*
Varietal Denomination: FUSION WHITE

(71) Applicant: Taiyan Yam, Apopka, FL (US)

(72) Inventor: Taiyan Yam, Apopka, FL (US)

( * ) Notice: Subject to any disclaimer, the term of this patent is extended or adjusted under 35 U.S.C. 154(b) by 125 days.

(21) Appl. No.: 13/987,702

(22) Filed: Aug. 21, 2013

(51) Int. Cl.
*A01H 5/00* (2006.01)

(52) U.S. Cl.
USPC ..... Plt./375

(58) Field of Classification Search
USPC ..... Plt./375
See application file for complete search history.

*Primary Examiner* — Keith Robinson
(74) *Attorney, Agent, or Firm* — Cassandra Bright

(57) ABSTRACT

A new and distinct *Calathea* cultivar named 'FUSION WHITE' is disclosed, characterized by showy green, light green and white patchy and marbled variegation. Plants are compact and easily produce side shoots. The new variety is commercially suitable for four inch, six inch and eight inch pot production. The new variety is an *Calathea*, typically produced as an indoor ornamental plant.

1 Drawing Sheet

Latin name of the genus and species: *Calathea leitzei.*
Variety denomination: 'FUSION WHITE'.

BACKGROUND OF THE INVENTION

The new cultivar is a product of chance discovery by the inventor Taiyan Yam. The discovery resulting in this new variety was made May 2007 at a commercial nursery in Malaysia. The interesting whole plant mutation was identified in a commercial planting of an unnamed, unpatented variety of *Calathea lietzei.*

Asexual reproduction of the new cultivar 'FUSION WHITE' was first performed at a commercial nursery in Malaysia by vegetative cuttings in 2007. Plants were tested and evaluated for 2 years to determine the stability of the variegation. During the propagation testing period, plants showed consistent stability of the interesting variegation. Subsequently the inventor confidentially tested the variegation for stability as finished plants at his nursery in Apopka, Fla. during 2010 through 2012. Production of finished plants has also shown that the unique features of this cultivar are stable and reproduced true to type.

SUMMARY OF THE INVENTION

The cultivar 'FUSION WHITE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'FUSION WHITE'. These characteristics in combination distinguish 'FUSION WHITE' as a new and distinct *Calathea* cultivar:

1. Showy variegated and marbled green and white coloration of the upper leaf surface.
2. Attractive compact plant.
3. Purple coloration to under leaf
4. Young foliage is characteristically heavily undulating.
5. Acute to acuminate leaf apex.
6. Each leaf has a different variegation pattern.

PARENT COMPARISON

Plants of the new cultivar 'FUSION WHITE' are similar to the unpatented parent *Calathea lietzei* in most horticultural characteristics. The new variety however differs in the following characteristics:

1. 'FUSION WHITE' has a foliage variegation not found on the parent variety. *Calathea lietzei* has a moderate light green and dark green variegation, whereas 'FUSION WHITE' has multiple shades of green and a strong white variegation.
2. 'FUSION WHITE' is a more compact plant, with more controlled, less vigorous growth.
3. 'FUSION WHITE' has a smaller leaf.

COMMERCIAL COMPARISON

'FUSION WHITE' can be compared to the unpatented commercial variety *Calathea* 'Freddie'. Plants of 'Freddie' are similar to plants of 'FUSION WHITE' in most horticultural characteristics. However 'FUSION WHITE' differs from 'Freddie' in the following characteristics:

1. 'FUSION WHITE' is a less upright plant than 'Freddie'.
2. 'FUSION WHITE' has foliage variegation of various shades of green and white, whereas plants of 'Freddie' have foliage variegation which is green and dark green.
3. 'FUSION WHITE' plants produce foliage variegation which varies considerably among the different leaves, whereas plants of 'Freddie' produce the same variegation pattern on every leaf.
4. Plants of 'FUSION WHITE' produce side shoots vigorously from and early age, whereas plants of 'Freddie' produce side shoots on a limited basis.

'FUSION WHITE' can be compared to the patented commercial variety *Calathea rosea picta* 'Dottie', U.S. Plant Pat. No. 12,736. Plants of *Calathea* 'Dottie' are similar to plants of 'FUSION WHITE' in most horticultural characteristics.

However 'FUSION WHITE' differs from *Calathea* 'Dottie' in the following characteristics:

1. Plants of 'FUSION WHITE' have less tolerance for high light levels than plants of 'Dottie'.
2. 'FUSION WHITE' has foliage variegation of various shades of green and white, whereas plants of 'Dottie' have foliage variegation which is dark green and pink.
3. 'FUSION WHITE' plants produce foliage variegation which varies considerably among the different leaves, whereas plants of 'Dottie' produce the same variegation pattern on almost every leaf.
4. Foliage of 'FUSION WHITE' is light purple on the underside, whereas 'Dottie' has foliage which is dark purple to red on the underside.

BRIEF DESCRIPTION OF THE PHOTOGRAPH

The accompanying photograph in FIG. 1 illustrates in full color a typical plant of 'FUSION WHITE' grown in a greenhouse in Apopka, Fla. This plant is approximately 8 months old, shown in a 6 inch pot.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'FUSION WHITE' plants grown in a polyhouse in Apopka, Fla., USA. Temperatures ranged from 80° F. to 90° F. during the day, 55° F. to 70° F. at night. No artificial light, photoperiodic treatments were given to the plants. For the first 2 months, plants were grown in shade, resulting in approximately 350 to 550 foot candles of light. After 2 months, the heavy shade is removed, and plants are finished at a natural light condition which varies between 550 to 10,000 foot candles. Measurements and numerical values represent averages of typical plant types.

Botanical classification: *Calathea leitzei* 'FUSION WHITE'.

Age of plant described: 240 days from a rooted cutting.

PROPAGATION

Time to initiate roots: Summer: 30 to 40 days at approximately 85° F. Winter: 40 to 50 days at approximately 64° F.

Root description: Roots emerge from nodes in rhizomes. Roots approximately 0.3 cm thick, colored near RHS White 155A. Rhizomes Green-White 157A, irregular oblong, approximate diameter range from 0.5 cm to 1.3 cm. Length varies with age, typically 1.0 cm to 3.0 cm.

Time to produce a young plant: From division cuttings to a 72 cell pack takes approximately 12 to 16 weeks. The variance in time depends upon the time of year.

PLANT

Growth habit: Compact, growth. Basal leaves emerge in clumps.

Pot size of plant described: 6 inches.

Growth rate: A finished 4 inch commercial pot can be produced in 4 to 5 months from a rooted 72 cell plug cutting. A 6 inch commercial pot can be produced in 7 to 8 months from a rooted 72 cell plug cutting.

Plant vigor: Slightly less than moderate, as typical with strongly variegated plants.

Plant shape: Upright, slightly outwardly arching, forming an irregular oval.

Height: 17 inches.

Plant spread: 16 inches.

Main stem color: Near RHS Yellow-Green 144C.

Main stem texture: Smooth.

Main stem length: Average range 8 to 10 inches.

Main stem diameter: Average approximately 0.5 cm.

Main stem strength: Flexible, easily resists breaking.

Branching characteristics: No true branching. Leaves emerge direct from base of plant.

Number of clumps of leaves: 4 to 8 clumps.

Number of leaves per clump: Average 4 to 8.

Age of plant described: 240 days from a rooted cutting.

Internodes: Not present. Individual stems arise from the rhizomes. No branching.

FOLIAGE

Leaf:

*Arrangement.*—Single leaves emerging basally, in clumping rosettes. No leaf internode.

*Quantity per stem.*—2 to 3.

*Average length.*—7 inches.

*Average width.*—2.5 inches.

*Shape of blade.*—Somewhat broad elliptic.

*Aspect.*—Slightly undulating.

*Apex.*—Acute to slightly acuminate.

*Base.*—Rounded.

*Margin.*—Entire.

*Appearance.*—Semi-glossy.

*Texture of top surface.*—Smooth.

*Texture of bottom surface.*—Smooth.

*Color.*—Mature foliage upper side: Near RHS Green 137A, 139A, 137C, 138B, Greyed-Green 193B, White N155B. All colors present individually in irregular patches and marbled variegations. Mature foliage under side: Near RHS Purple N79D.

Venation:

*Type.*—Pinnate.

*Venation coloration upper side.*—Indistinguishable from leaf blade coloration.

*Venation coloration under side.*—Indistinguishable from leaf blade coloration.

Petiole:

*Length.*—6 inches.

*Diameter.*—Approximately 0.5 inches.

*Color.*—Near RHS Green 138C.

*Texture.*—Smooth.

Petiole sheath:

*Length.*—Approximately 1 to 1.5 inches.

*Diameter.*—Approximately 0.8 inches.

*Color.*—Near RHS Green 138C and Green-White 157A.

*Texture.*—Smooth.

FLOWERS

Not observed to date and not typically producing flowers.

OTHER CHARACTERISTICS

Disease and pest resistance: Typical resistance and susceptibility to normal pests and diseases of *Calathea* has been observed. Typical diseases found in the Marantaceae family include: *Pseudomonas* species, *Pseudomonas cichorii, Alternaria alternata, Fusarium oxysporum.* Typical pests include: *Radopholus similis, Tetranychus urticae,* and various flies from the Sciaridae family.

Drought tolerance and cold tolerance: The new cultivar is a typical *Calathea*, cold tolerant to approximately 55° F. and does not tolerate drought. High temperature tolerance to at least 90° F.

Fruit/seed production: Not observed.

What is claimed is:

1. A new and distinct cultivar of *Calathea* plant named 'FUSION WHITE' as herein illustrated and described.

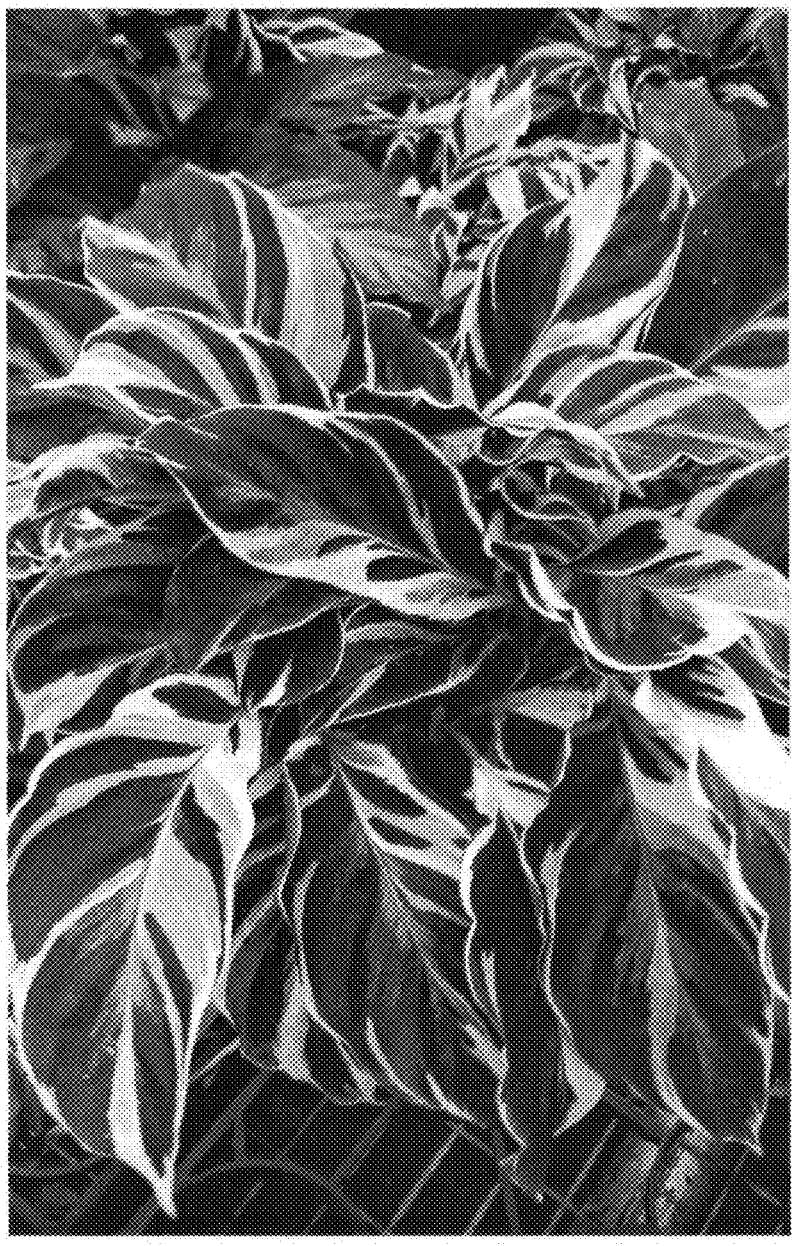

* * * * *